(12) United States Patent
Neumann et al.

(10) Patent No.: US 10,436,769 B2
(45) Date of Patent: Oct. 8, 2019

(54) METHOD, APPARATUS, AND COMPUTER PROGRAM FOR MONITORING BREATH

(71) Applicant: Dräger Safety AG & Co. KGaA, Lübeck (DE)

(72) Inventors: Ingo Neumann, Bad Oldesloe (DE); Alexander Sarcinelli, Ahrensburg (DE); Matthias Willner, Lübeck (DE)

(73) Assignee: Dräger Safety AG & Co. KGaA, Lübeck (DE)

( * ) Notice: Subject to any disclaimer, the term of this patent is extended or adjusted under 35 U.S.C. 154(b) by 215 days.

(21) Appl. No.: 15/342,516

(22) Filed: Nov. 3, 2016

(65) Prior Publication Data

US 2018/0120293 A1 May 3, 2018

(51) Int. Cl.
*G01N 33/497* (2006.01)
*A61B 5/091* (2006.01)

(52) U.S. Cl.
CPC ......... *G01N 33/4972* (2013.01); *A61B 5/091* (2013.01)

(58) Field of Classification Search
CPC ............................ G01N 33/4972; A61B 5/091
USPC ....................................................... 73/23.3
See application file for complete search history.

(56) References Cited

U.S. PATENT DOCUMENTS

| 4,984,158 A * | 1/1991 | Hillsman ............... A61B 5/087 128/200.14 |
| 9,417,232 B2 * | 8/2016 | Keays ................... B60K 28/063 |
| 2003/0176803 A1 * | 9/2003 | Gollar .................... A61B 5/097 600/532 |
| 2014/0062682 A1 * | 3/2014 | Birnbaum ................ G08B 6/00 340/407.2 |
| 2014/0165697 A1 * | 6/2014 | Mochizuki ......... G01N 33/4972 73/23.3 |
| 2014/0335905 A1 * | 11/2014 | Bhoot ..................... H04W 4/02 455/466 |
| 2016/0371590 A1 * | 12/2016 | Blackley ................. G06N 5/04 |

* cited by examiner

*Primary Examiner* — Marrit Eyassu
(74) *Attorney, Agent, or Firm* — McGlew and Tuttle, P.C.

(57) ABSTRACT

A method for monitoring breath is provided, comprising: measuring one or more attributes of airflow through an input device, by a flow sensor within the input device, of air blown into said input device by an expelling action of a user; transmitting the attributes of airflow from the input device to a processing device, including a processor and communication terminal; communicating, via the communication terminal, a first state output to the user while the air is blown into said input device; and determining, by the processor of the processing device, whether each of the attributes of airflow is within a respective threshold range. If a respective threshold range is met, the communication terminal communicates a second state output to the user.

20 Claims, 12 Drawing Sheets

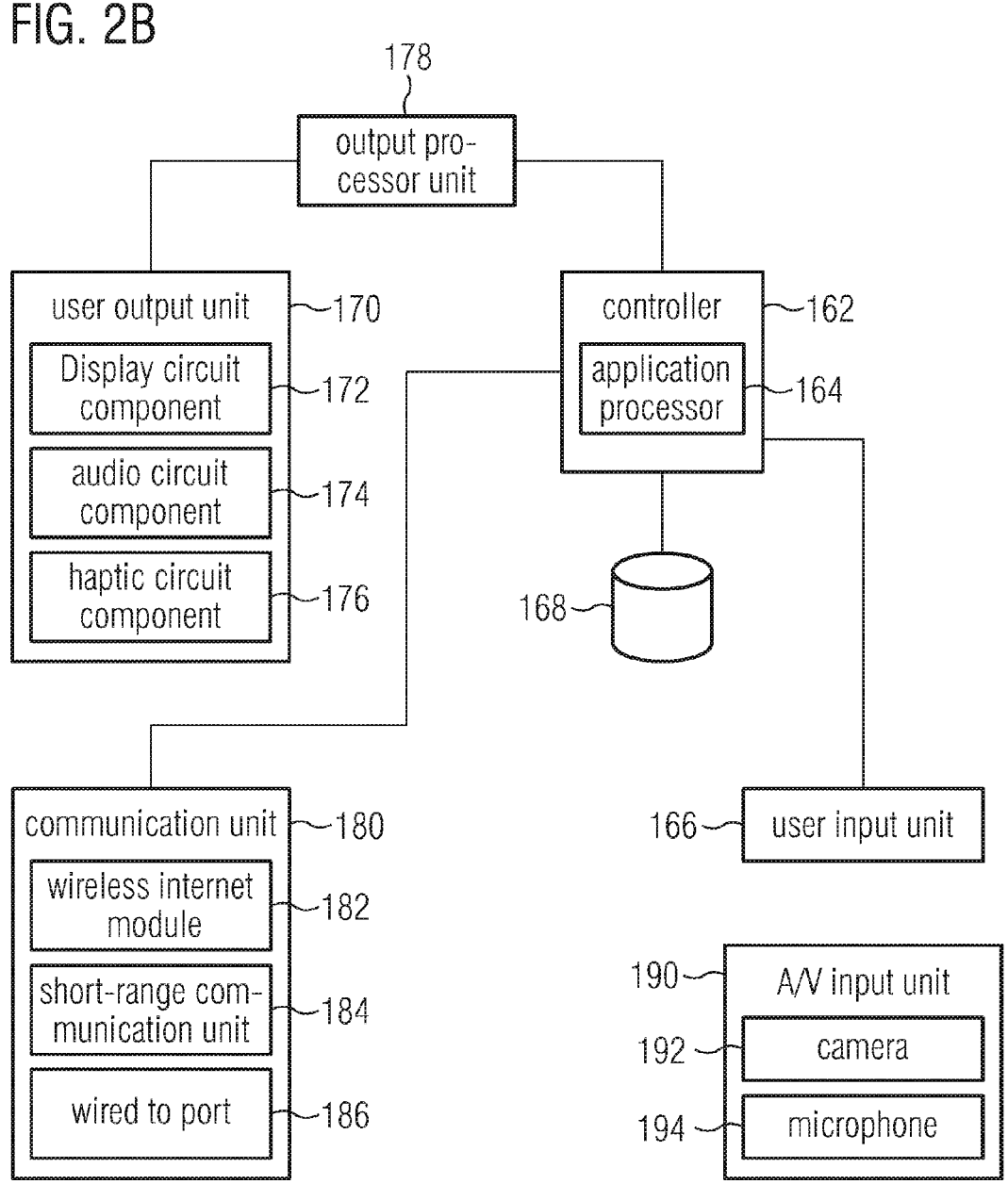

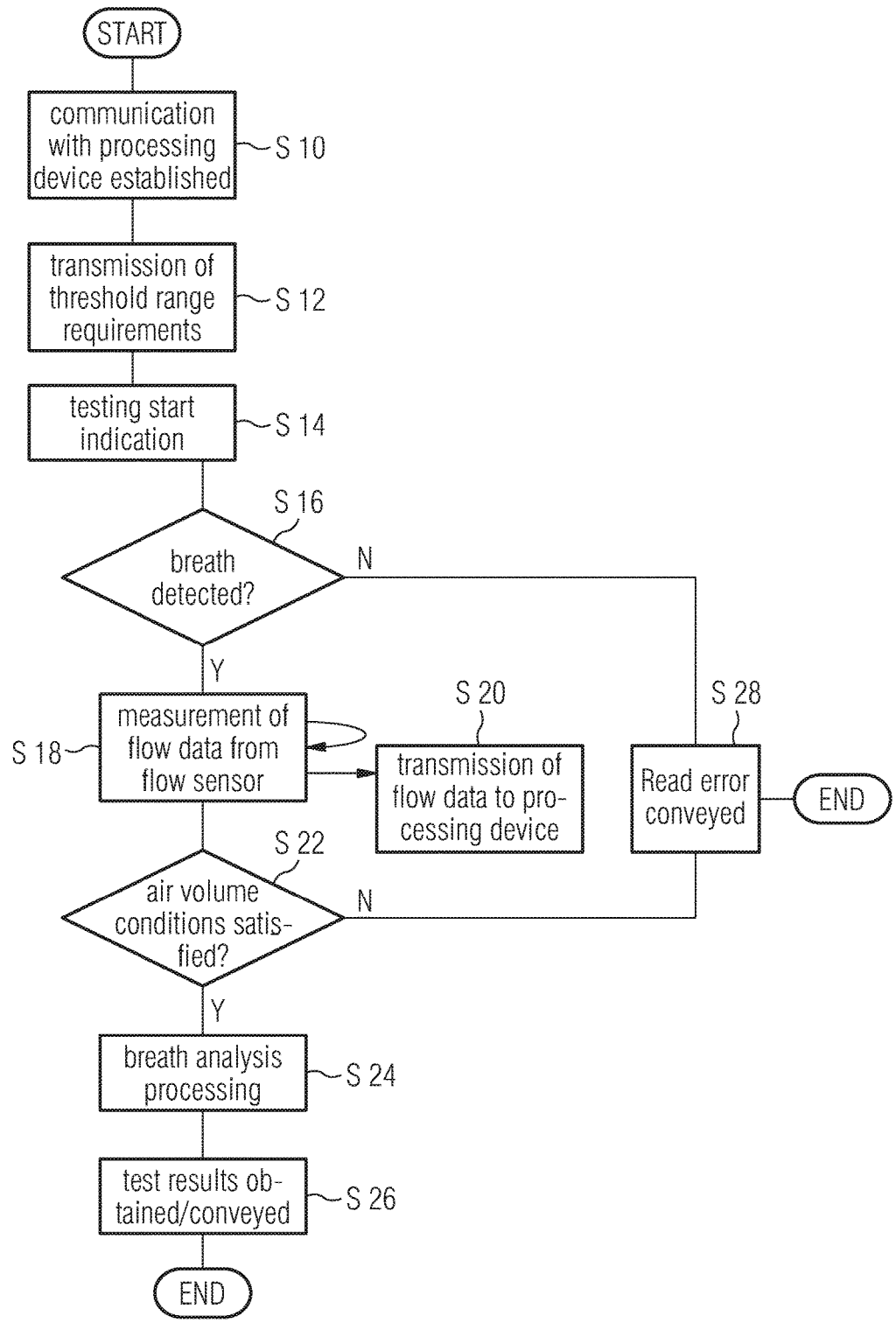

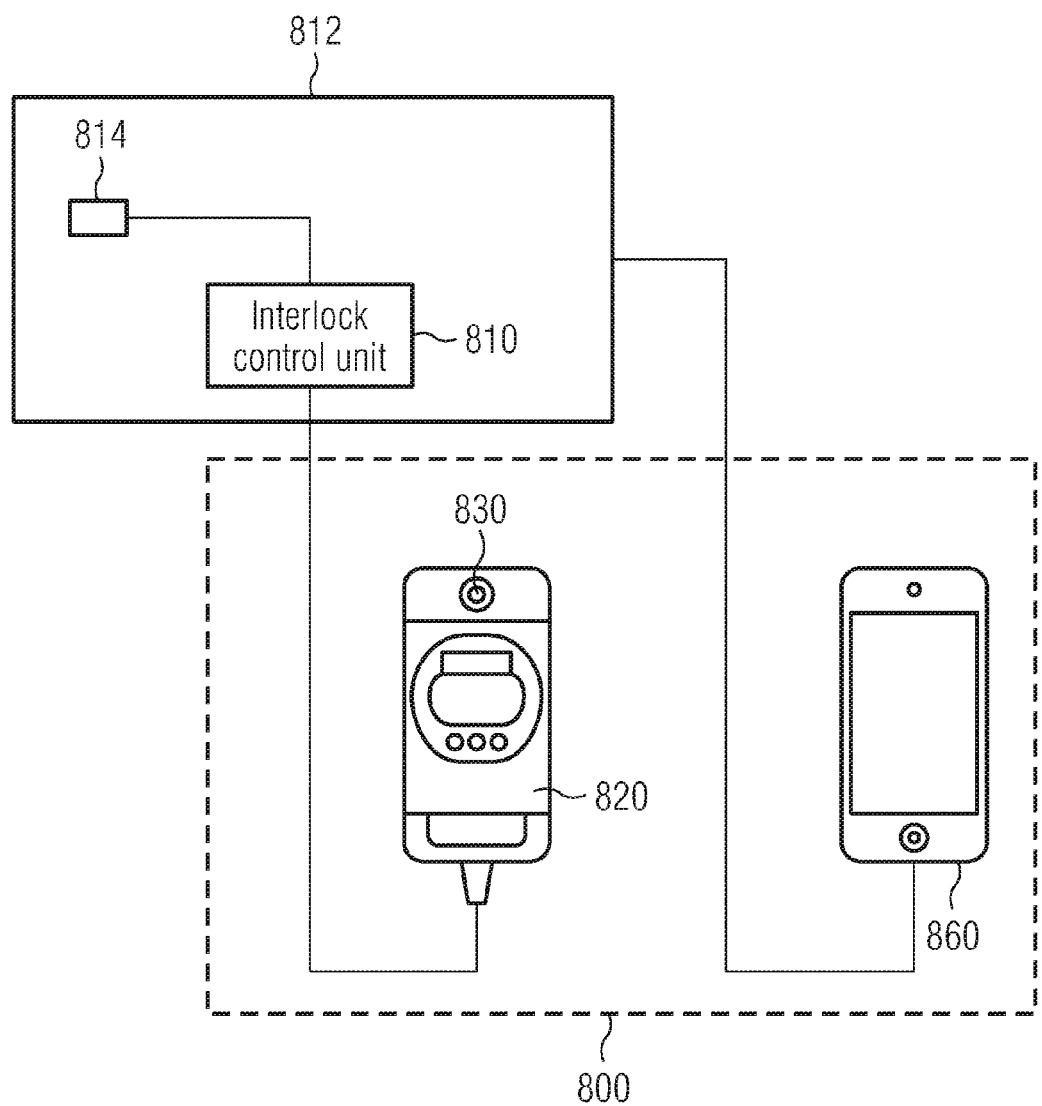

METHOD, APPARATUS, AND COMPUTER PROGRAM FOR MONITORING BREATH

FIELD

The present disclosure is directed to methods and apparatuses for monitoring breath, and a computer program, which can, in some implementations, execute information processing for simplification of breath alcohol determination.

BACKGROUND

Currently, there has been a consorted effort to dampen the effects of intoxication on day to day life. Modern initiatives have been made to curb such behavior and make scientific measurement of intoxication more accessible to the general public. "Breath alcohol determination" refers to the measurement of alcoholic content in the breath, after consumption of alcoholic beverages, food, or the like. The scientific basis for such determination is made through a gas exchange, which takes place in the pulmonary alveoli between the breath and the consumed alcohol. Any alcohol contained in the peripheral blood is absorbed by fresh air inhaled by a person and is thus emitted by that person together with exhaled air. It is thus that alcohol measurement may be carried out and the level of blood alcohol of a person may be ascertained.

Generally, a breath monitoring system will perform the aforementioned actions to measure blood alcohol concentration (BAC) levels on the breath. Nowadays, there exist a number of portable, handheld, and stationary breath monitoring systems (herein also known as "breathalyzers," "blood alcohol testers," "BAC trackers," etc.) to determine the level of alcohol in the breath. By carrying out measurements using electro-chemical or physical parameters, the alcohol value in the breath is calculated and is typically shown by a display. Such systems are especially applicable during alcohol-level roadside checks carried out by the law enforcement. Though, it is also the case where alcohol testers are employed for private use or in work areas, e.g., in the medical field in detoxification centers, workplace drug testing areas, etc.

However, several disadvantages of these systems are known in the art. One such disadvantage is that instruction of proper testing is not intuitive to a user. Often times, a user will test her/his blood alcohol level but fail to meet the proper operational requirements of the breathalyzer. For example, a user will blow too forcefully or not forceful enough, or for too little time. This results in read errors, which, in turn, cause delays, e.g., of the system having to reset for subsequent testing. In turn, a user may feel anxious, due to testing delays or testing anxiety, and may experience further stigmas associated with giving an improper sample. Such stigma is borne from the motivation to give the sample initially, whether per requirements or for personal use to overcome one's own addiction.

SUMMARY

A new and novel system and method is presented in view of the forgoing. The present disclosure provides a new and novel system and method for proper breath testing as facilitated by various existing and future interactive devices, such as but not limited to, mobile phones, car navigation systems, personal computers and tablets, etc.

According to an example of the disclosure, a method is provided for monitoring breath. The method comprises measuring one or more attributes of airflow through an input device, by a flow sensor within the input device, of air blown into said input device by an expelling action of a user; transmitting the attributes of airflow from the input device to a processing device, including a processor and communication terminal; communicating, via the communication terminal, a first state output to the user while the air is blown into said input device; and determining, by the processor of the processing device, whether each of the attributes of airflow is within a respective threshold range. If a respective threshold range is met, the communication terminal communicates a second state output to the user.

In some examples, the attributes of airflow measured by the flow sensor can include at least the volume of air or the duration of time air is blown, as detected by the flow sensor. In still another example, the method can also include an initial act of transmitting initialization data, including the respective threshold range of an attribute of airflow, from the input device to the processing device before measuring said attribute of airflow from the input device.

According to another example of the present disclosure, there is provided a mobile terminal for monitoring breath. The mobile terminal includes an I/O processing circuit component that receives transmission of attributes of airflow from an input device, including a flow sensor, of air blown into said input device by an expelling action of a user. The mobile terminal also includes: a communication terminal, which includes an interface circuit and communicates, via the interface circuit, a first state output to the user while air is blown into said input device; and a processor, which processes whether each of the attributes of airflow is within a respective threshold range. If a respective threshold range is met, the processor transmits to the communication terminal validation of a met threshold range, and the communication terminal communicates via the interface circuit a second state output to a user.

According to another example of the present disclosure, there is provided a computer program for a computer. The computer program comprises instructions that, when executed on a processor, perform the steps of: receiving an electronic transmission of one or more attributes of airflow from an input device, which measures the attributes of airflow by a flow sensor within the input device of air blown into said input device by an expelling action of a user, to a mobile device, including the processor and a communication terminal; communicating, via the communication terminal, a first state output to the user while the air is blown into said input device; and determining, by the processor, whether each of the attributes of airflow is within a respective threshold range. If a respective threshold range is met, the communication terminal communicates a second state output to the user.

What is obtained by translating arbitrary combinations of the above constituent elements and expressions of the present disclosure among method, device, system, recording medium, computer program, and so forth is also effective as an example of the present disclosure.

According to examples of the present disclosure, a testing environment is achieved, whereby a user's breath, e.g., for testing blood alcohol in a breathalyzer system, may be properly and accurately measured. With the present disclosure, improper testing will decrease and testing stigma may decrease, leading to the acceptance for alcohol testers and/or simplification of giving a sample. For this purpose, a customer-friendly animation on a display is to enable precise and playful handling of alcohol testers, thus making alcohol testers more attractive and accepted within all markets, including medical and law enforcement markets, markets of "breath alcohol ignition interlock devices," and the "home monitoring" market, as well as for the private market.

BRIEF DESCRIPTION OF THE FIGURES

Some examples of apparatuses and/or methods will be described in the following by way of example only, and with reference to the accompanying figures, in which

FIG. 2B is a diagram showing the functional block configuration of a processing device in the example;

FIG. 3 is a state flowchart showing the procedure of the input device communicating and analyzing breath detection and measurement in the example;

FIG. 11 is a diagram showing a blood alcohol content (BAC) processing system of a breath alcohol ignition interlock device in another example of the present disclosure;

DETAILED DESCRIPTION

Various examples will now be described more fully with reference to the accompanying drawings in which some examples are illustrated. In the figures, the thicknesses of lines, layers and/or regions may be exaggerated for clarity.

Accordingly, while further examples are capable of various modifications and alternative forms, some particular examples thereof are shown in the figures and will subsequently be described in detail. However, this detailed description does not limit further examples to the particular forms described. Further examples may cover all modifications, equivalents, and alternatives falling within the scope of the disclosure. Like numbers refer to like or similar elements throughout the description of the figures, which may be implemented identically or in modified form when compared to one another while providing for the same or a similar functionality.

It will be understood that when an element is referred to as being "connected" or "coupled" to another element, the elements may be directly connected or coupled or connected via one or more intervening elements. If two elements A and B are combined using an "or," this is to be understood to be a "logical or," disclosing all possible combinations, i.e., only A, only B, as well as A and B. An alternative wording for the same combinations is "at least one of A and B. The same applies for combinations of more than two Elements.

The terminology used herein for the purpose of describing particular examples is not intended to be limiting for further examples. Whenever a singular form such as "a," "an," and "the" is used and using only a single element is neither explicitly or implicitly defined as being mandatory, further examples may also use plural elements to implement the same functionality. Likewise, when a functionality is subsequently described as being implemented using multiple elements, further examples may implement the same functionality using a single element or processing entity. It will be further understood that the terms "comprises," "comprising," "includes," and/or "including," when used, specify the presence of the stated features, integers, steps, operations, processes, acts, elements and/or components, but do not preclude the presence or addition of one or more other features, integers, steps, operations, processes, acts, elements, components and/or any group thereof.

Unless otherwise defined, all terms (including technical and scientific terms) are used herein in their ordinary meaning of the art to which the examples belong.

Figure 1:
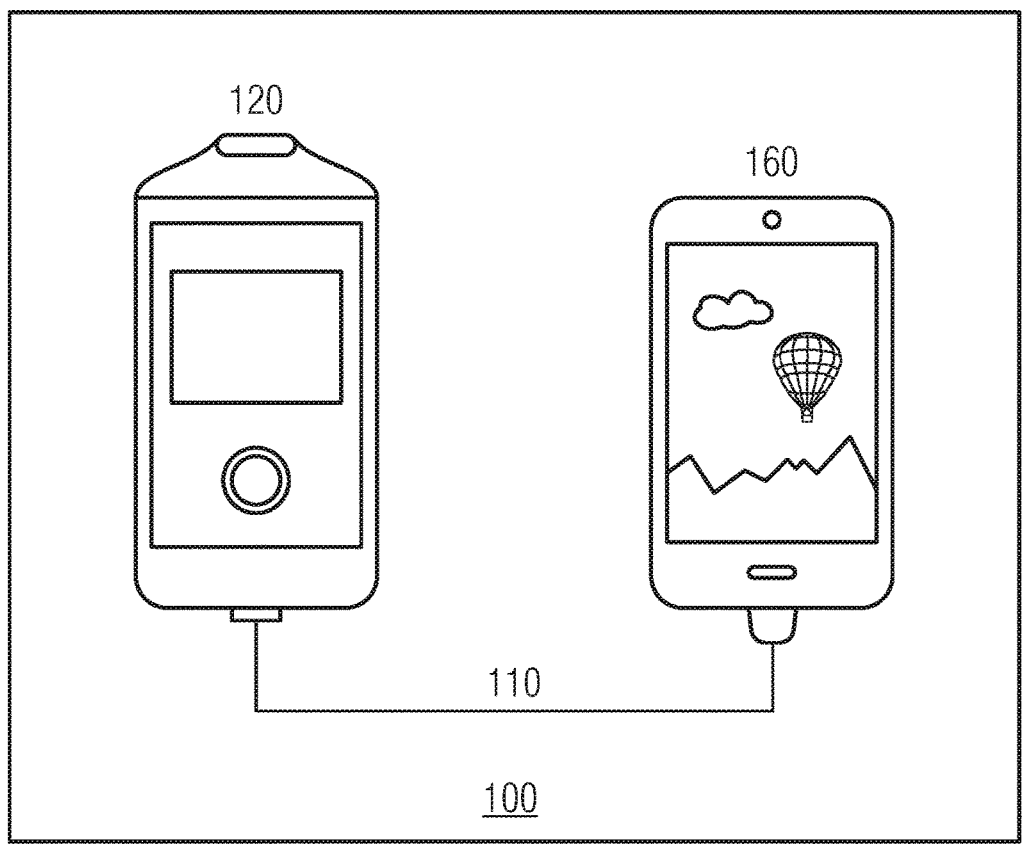
FIG. 1 is a diagram showing a blood alcohol content (BAC) processing system in an example of the present disclosure.

FIG. 1 shows a blood alcohol content (BAC) processing system 100 according to an example of the present disclosure. The BAC processing system includes an input device 120 and a processing device 160. The input device 120 interacts with the processing device 160 such that electronic information is received and transmitted between said devices. The present example shows a wired connection 110 between said devices, creating an information exchange circuit by which data is conveyed.

Figure 2A:
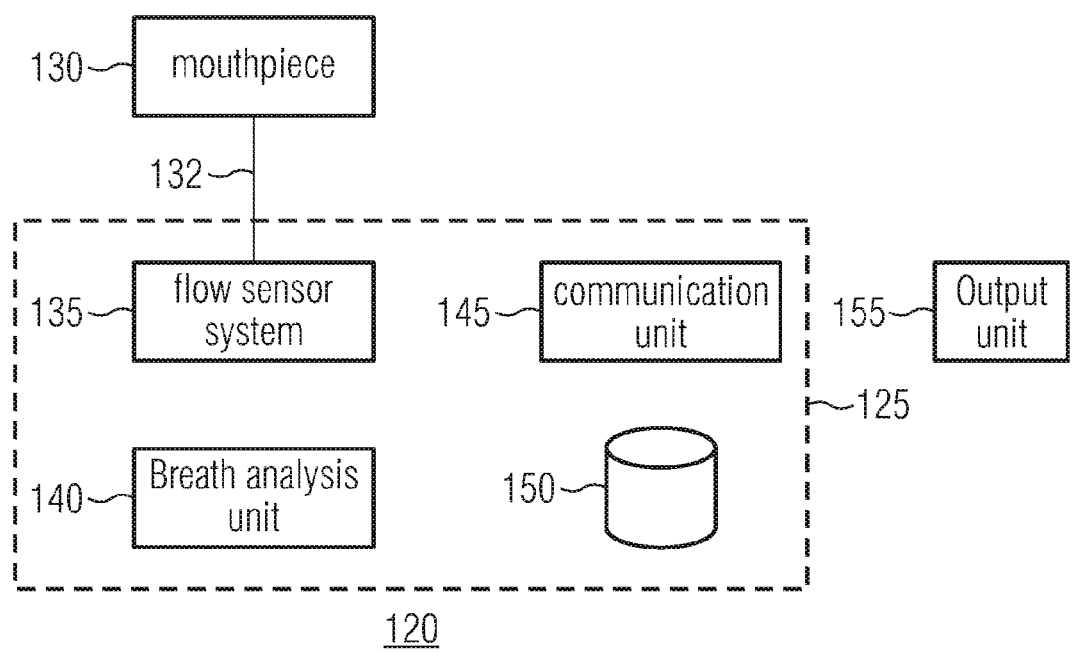
FIG. 2A is a diagram showing the functional block configuration of an input device in the example.

FIG. 2A shows the input device 120 of an example in the present disclosure. The input device 120 is a breath-alcohol measuring device, such as a breathalyzer or Breathometer; it serves as a means by which blood alcohol content of a person is measured. The input device of the present example comprises a mouthpiece 130, a flow sensor system 135, a breath analysis unit 140, a communication unit 145, memory 150, and an output unit 155.

The mouthpiece 130 of the input device 120 is conveyed to receive a volume of respiratory gas that is exhaled by a person, a user of the BAC processing system 100, to be measured. As captured breath flows through a flow channel 132, a flow sensor system 135 detects various attributes of the breath. A flow sensor system 135 is part of the internal configuration 125 of the input device 120 and may be one or a combination of sensors to detect properties of the air flown into said input device 120. For example, the flow sensor system 135 may have a pressure sensor, temperature sensor, or the like to detect the pressure and temperature, respectively, of airflow received by the mouthpiece.

In the example of the present disclosure, the flow sensor system 135 has means to detect: the volume of air that is blown into the mouthpiece; the pressure of airflow of the air blown; or the duration of time air is blown into the mouthpiece; from a single exhalation by a user. Subsequently, it is determined whether the flow sensor system 135 has detected a proper sample of exhaled respiratory gas. A proper sample would be, for example, a sample that was given with enough air volume to determine blood alcohol levels, given at a duration of time that was not too short. An improper sample would be a sample that was given with not enough air volume, or a volume of air that was blown too quickly, thus resulting in too much air pressure detecting in the system.

It should be noted that what is considered a proper or improper air sample is based on threshold range requirements determined by each input device. That is, the input device 120 of the example of FIG. 1 may have a different threshold for, e.g., volume of airflow, than another example of the present disclosure. Memory storage 150 is provided as part of the internal configuration 125, which allows for storage of initialization information, such as threshold range requirements. It is noted that the threshold range requirements determined by the input device relate to the air sample needed to successfully measure the blood alcohol level of a user and are not directed to the blood alcohol level measurement itself, which may not be device-specific and may be set according to law enforcement standards or according to personal/private use goals.

The volume of air that is blown may be evaluated by the breath analysis unit 140 to determine the blood alcohol concentration of the sample of air. If the flow sensor system 135 detects a proper sample, then the breath analysis unit 140 may adequately detect the blood alcohol concentration of the sample; if an improper sample is detected by the flow sensor system 135, then the breath analysis unit 140 will have an inadequate sample and thus give incorrect information or be unable to make a determination, thus resulting in read errors or the like.

The breath analysis unit 140 determines the result, i.e., the percentage of blood alcohol concentration, of the sample of airflow. The output unit 155 may be a display panel, audio unit, or a combination of audio/visual communication means to convey to the user the result of the breath analysis unit 140. The output unit 155 may also prompt a user to give a sample of air for initial or retesting, or may signal to a user that there was a read error, through audio or visual communication means.

The input device 120 may also convey, e.g., the result of the sample of airflow to another device external to the input device 120, through the communication unit 145. The communication unit 145 may include an I/O port for receiving and transmitting input and output of the input device 120 to the processing device 160. It is noted that the example of the present disclosure shows a wired communication means between the two devices. However, it can be appreciated by those skilled in the art that the connection from the input device need not be wired. Instead, the communication unit 145 may transmit and receive data via a wireless signal connection protocol or by a short-range communication protocol. That is, the input device 120 may have a wireless antenna, capable of using mobile networking and Internet protocols such as Wi-Fi, LTE, GSM, or the like, or a short-range antenna capable of short-range communications via Bluetooth, radio frequency (RF) waves, among others. Further it may be appreciated that the input device 120 may be integrated with the processing device 160, as described in a later embodiment.

The input device 120 is capable of communicating information to the processing device 160, as shown in FIG. 2B. The processing device may be a mobile terminal such as a mobile phone, a tablet, or a personal computer, a car navigational system, or any means that serves as an interaction device between digital information and a user. In the example of the present disclosure, the processing device 160 is a mobile phone terminal.

The processing device 160 includes a controller 162, which is a functional unit that controls the mobile phone system and that comprises an application processor 164, representative of and functionally disposed to run and process software applications, e.g., computer programs or software code, on the processing device 160. The processing device 160 also includes a user input unit 166, to detect and retrieve user input in the form of, e.g., keyboard strokes or button pushes, and a memory 168, which stores data such as software applications, system information, and the like.

The processing device 160 further includes a user output unit 170 for conveying information to a user. The user output unit 170 may include: a display circuit component 172, such as a display or screen, for displaying visual communication to a user; an audio circuit component 174, such as an audio output module or speakers, for conveying auditory communication to the user; or a haptic circuit component, such as a vibration unit or other tactile effects component, for conveying kinesthetic communication to the user. The display circuit component may include known display technologies, such as LCD or OLED screens, for example. The processing device 160 of the present disclosure includes a display.

An output processor unit 178 is a dedicated processor for accelerating and arranging output information to be conveyed by the user output unit 170. For example, the output processor unit 178 is a specialized circuit accelerates image output for a display. The application processor 164 works with the output processor unit 178, e.g., to properly run and display a software application on the processing device 160. An audio visual (A/V) input unit 190 also may be provided with a camera 192 and microphone 194. The A/V input unit 190 provides input in the form of audio or visual signals to the processing device 160. The camera 192 provided receives external visual environment information and processes such by image sensors as image frames for pictures or video. Likewise, the microphone 194 receives external audio environment information and processes such as electronic audio information.

The processing device also includes a communication unit 180 to communicate with electronic devices external to the communication unit. The communication unit 180 may include means for establishing a communication circuit, such as with a wireless internet module 182, a short-range communication module 184, or a wired I/O port 186.

The example of the present disclosure allows for the input device 120 to transmit information regarding the captured sample of input airflow to the processing device 160. FIG. 3 shows a functional state flowchart diagram of the interaction between the input device 120 and the processing device 160, from the side of the input device 160.

As an initial step, the input device 120 establishes communication S10 with the processing device 160 through the respective communication units 145, 180 of each device. Once communication is established, the input device 120 transmits initialization information S12 to the processing device 160, such as input device system information or threshold range requirements that convey requisite attributes of airflow needed for a proper sample. For example, the input device 120 would convey the requisite volume of air or the requisite duration of time needed to be measured by the flow sensor system 135 in order to obtain a sample adequate enough to measure blood alcohol concentration effectively.

After initialization data is sent from the input device 120, the input device may give some example start indication S14, via graphical or audio means, for the user to breath into the mouthpiece 130 of the input device 120. If no breath is detected after a certain period of time, airflow conditions are not met, resulting in a read error S28. However, if breath is detected, the flow sensor system 135 measures the flow data S18 from the airflow provided by one exhalation of breath cycle by a user.

Concurrent to this, the communication unit 145 transmits information S20 of flow data, e.g., the attributes of airflow, to the processing device 160 in real-time, while airflow is detected. If the flow sensor system 135 determines S22 that the air volume conditions are satisfied, that is, that the threshold range of volume of air or the duration of time air is blown is met by the sample measurement, then breath analysis processing begins S24 and testing results are subsequently obtained S26. However, if the conditions are not met, a read error may be conveyed S28.

The processing device 160 has a software application that is started by a user in order to test the breath of a user for blood alcohol content evaluation. The software application is stored in memory 168 and executed by the application processor 164. When a user starts the application, the software application, through the output processor unit 178, configures the display circuit component 172 to display an initial screen to start the program for breath testing.

The processing device 160 may then prompt a user via the user output unit 170 to perform various tasks. For example, the processing device may be a smartphone, via which the smartphone display prompts the user to perform a breath test. The user may optionally be prompted by the software application to hold the smartphone, which has a front-facing display camera 192, by giving instruction in order to allow a picture to be taken of the user while she/he gives a breath sample via the input device 120.

As a breath sample is given or prompted to be given by a user through the input device 120, the user affirmatively presses a button (detected by the user input unit 166) that is displayed on the software application's user interface. It is then that a user may concurrently use the input device 120 and the processing device 160. Then, the software application displays, on the display circuit component 172, a screen as part of its user interface a first state 200. The user then blows into the mouthpiece 130 of the input device 120 while the first state 200 is displayed on the processing device 160.

Figure 4:
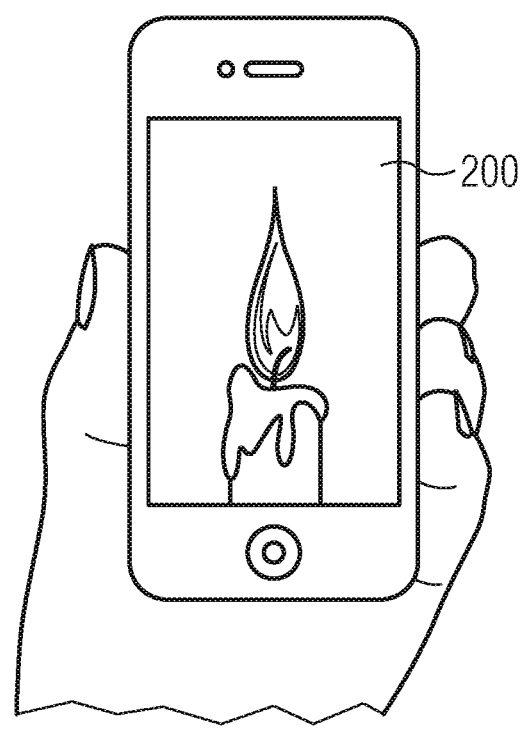
FIG. 4 is a diagram showing one example of a first state displayed by an application on the processing device.

FIG. 4 shows an example of a first state 200 of the software application of the processing device. The first state 200 is, e.g., a virtual or animated image depicting a theme, such as a candle with a flame. The theme displayed by the first state may relate to some image, action, or concept that involves air or breath, inflation, blowing, etc. The theme relates to an intuitive function of a user blowing into the input device 120. The theme may also be customizable, whereby the user may choose between a multitude of themes and preferences.

Figure 5:
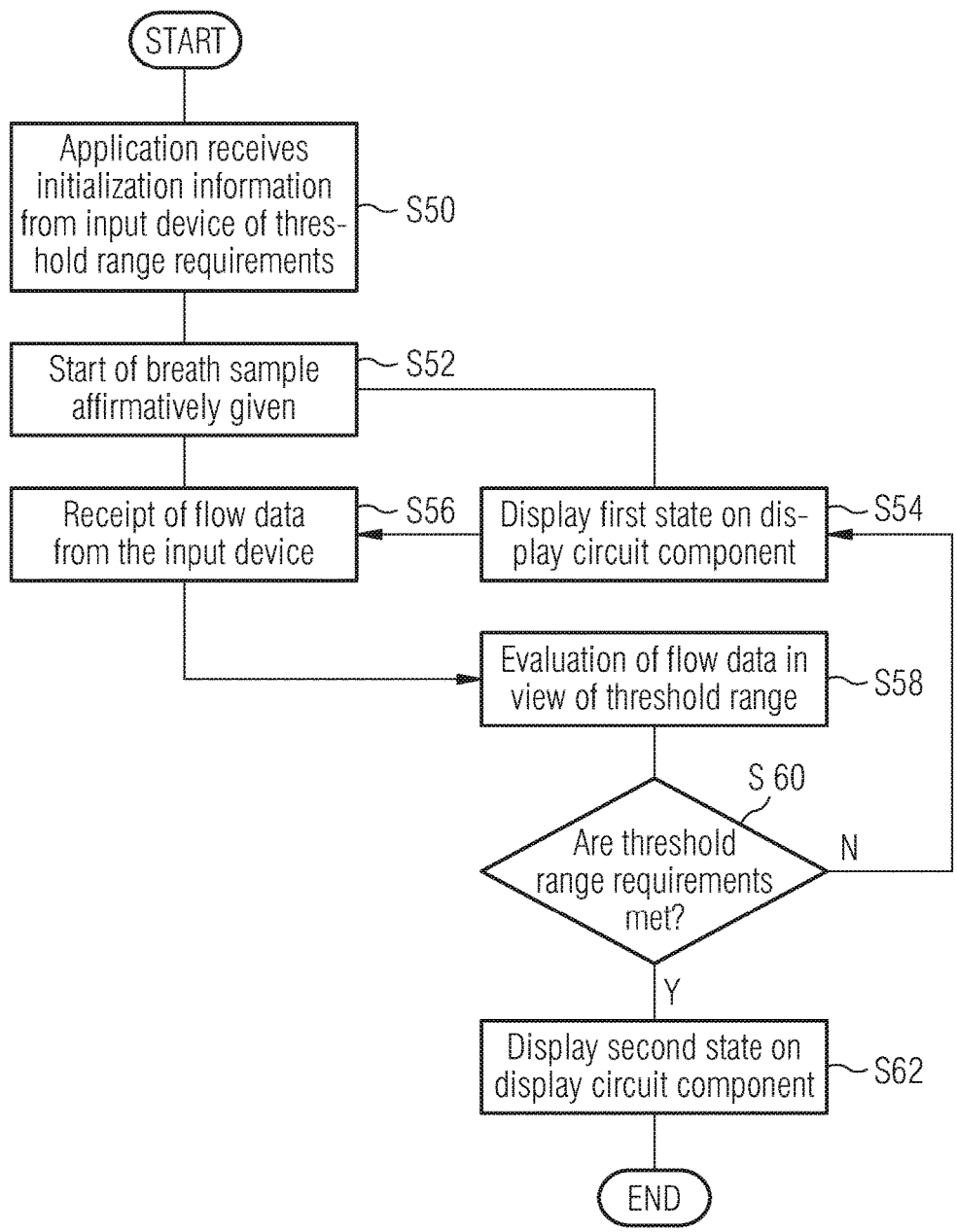
FIG. 5 is a state flowchart showing the procedure of the processing device receiving communication and interactively displaying breath measurement in the example.

The processing device 160 runs the software application while communicating with the input device 120. FIG. 5 shows a functional state flowchart diagram of the interaction between the processing device 160 and the input device 160, from the side of the processing device.

When the software application for analyzing breath is started, the application processor 164 initializes the software application, including receiving initialization information S50 from the input device 120 that was either stored in memory 168 or requested by the communication unit 180. The application further causes the output processor unit 178 to display a user interface on the display circuit component 172. As stated before, the initialization information conveys the threshold range requirements of the attributes of airflow, e.g., the volume of air or the duration of air blown that is needed for a proper sample. The threshold range requirements are stored into memory 168 by the software application. When a user affirmatively presses the button on the user interface to start a breath sample given S52, the first state 200 is displayed S54 on the display circuit component 172.

The processing device 160 then receives flow data from the input device 120 in the form of the aforementioned attributes of airflow. The receipt of flow data is in real time. That is, the software application can indicate that air is being blown into the mouthpiece 130 as the airflow is detected by the flow sensor system 135. The software application, by way of the application processor 164, performs evaluation S58 of the attributes of airflow, comparing the threshold range requirements stored in memory with those received by the input device 120.

If it is determined by the application processor 164, based on the instructions of the software application, that the threshold range requirements are met, that is, that the amount of air is of the requisite volume or given in the requisite duration of time for a proper sample to be evaluated, then the software application causes the output processor unit 178 to display a second state 300. If the attributes of airflow are not met, then the first state 200 will continued to be displayed.

Figure 6:
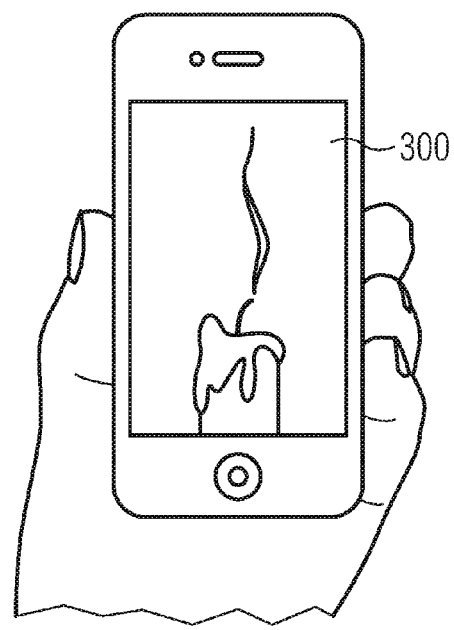
FIG. 6 is a diagram showing one example of a second state displayed by an application on the processing device.

FIG. 6 is an example of a second state 300 of the software application, also in the form of a virtual or animated image that is displayed on the display circuit component 172. As compared to the first state 200, the second state 300 shows a candle being blown out. The image of second state 300 intuitively conveys to a user that the breath given to the input device 120 was sufficient enough to blow the candle out.

Figure 7A:
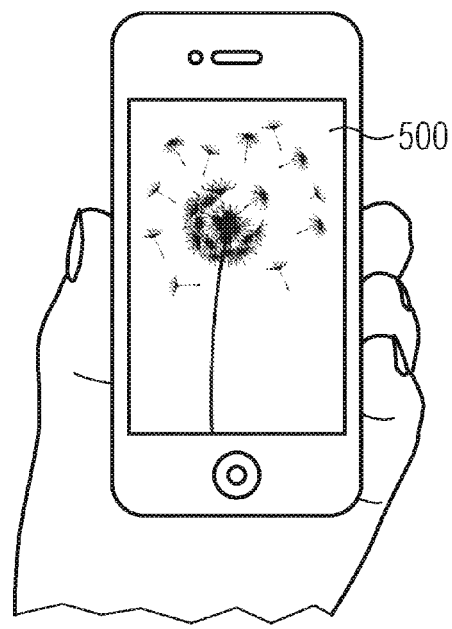
FIG. 7A is a diagram showing an example of an intermediary state displayed an application on the processing device.
Figure 7B:
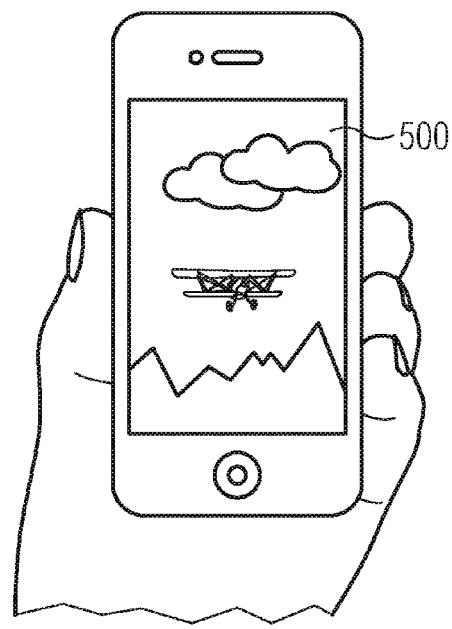
FIG. 7B is a diagram showing an example of an intermediary state displayed an application on the processing device.

It can be understood by those skilled in the art that the software application implements a state machine, by which determination is made to transition the first state 200 to the second state 300. It may also be appreciated by those skilled in the art that there may be one or more sub-states 500, e.g., virtual or animated images that convey information in between the first state 200 and second state 300. FIGS. 7A and 7B are further examples of the present disclosure of a plurality of sub-states 500 that the software application may display on the processing device 160, of different themes (such as a dandelion theme or a plane theme). The sub-states 500 may be determined by the software application, e.g., based on the difference between a current measure of an attribute of airflow and one of the bounds of the threshold range requirements stored.

Figure 8A:
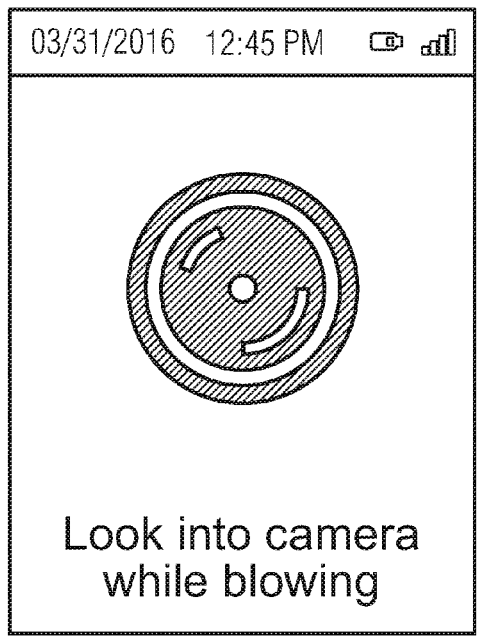
FIG. 8A is a diagram showing an example of an introduction state displayed by an application on the processing device.
Figure 8B:
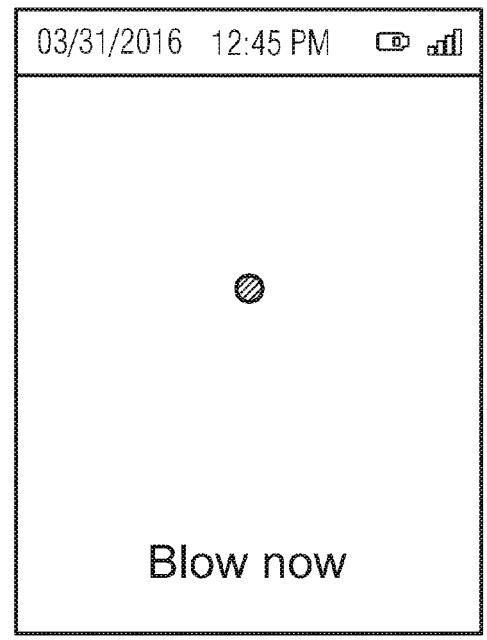
FIG. 8B is a diagram showing an example of a first state displayed by an application on the processing device.
Figure 8C:
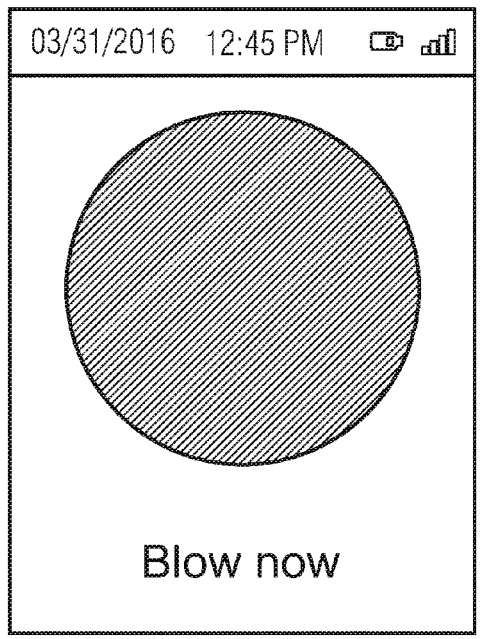
FIG. 8C is a diagram showing an example of a second state displayed by an application on the processing device.

Further, various sub-states may be present before or after the first and second state. For example, states that give feedback or states that give instruction may be displayed by the software application on the processing device 160. FIGS. 8A-8C show a sequence of states displayed on, e.g., a display. An initial or introductory state is given in FIG. 8A whereby a user is instructed to look into a camera device located within a processing device 160 and to blow. FIG. 8B represents a first state that shows a small circle, and FIG. 8C represents a second state of a large circle, otherwise considered an expanded circle of FIG. 8B. It can be understood by those skilled in the art that states may exist before, between, and after FIGS. 8B and 8C.

The sub-states 500 may also indicate processed measurements of the attributes of airflow themselves. For example, if a user blows too strongly or with too much air pressure into the input device 120, the candle of FIG. 4 may flicker strongly, as a sub-state 500. If the user blows weakly, the candle flame may hardly move. It is only when the desired volume and duration of sample given is reached will the candle be flown out (FIG. 6). The second state 300 shows that a proper sample has been given to the input device in a successful manner.

It may further be appreciated by those skilled in the art that the states need not be conveyed by the software application in a visual manner. Instead, the first state or second state, and/or the sub-states, if they exist, may be conveyed through auditory communication means, through the audio circuit component 174, or kinesthetic communication means, by the haptic circuit component. The states may be conveyed by combination of audio, visual, and kinesthetic communication.

Using the animation, sound, or vibration of each state, "correct" blowing by the user can be taught by the software application and thus be learned. As a result, the usual mistakes made when giving a sample can be avoided and the amount of unnecessary read errors by the input device 120 may decrease. Further, the user may feel enjoyment with the fun and playful aspects of the themes conveyed by the software application, and thus the stigma associated with testing may thus decrease.

The aforementioned is an example of a blood alcohol content processing system that utilizes a mobile device. However, the present disclosure may allow for a BAC processing system for a "breath alcohol ignition interlock device" used to lock the ignition of a car. For breath alcohol ignition interlock devices, when a user's breath is shown to be within a legal blood alcohol level range, the ignition of a car may unlock from a signal sent from an input device to the controls of an automobile.

Figure 9:
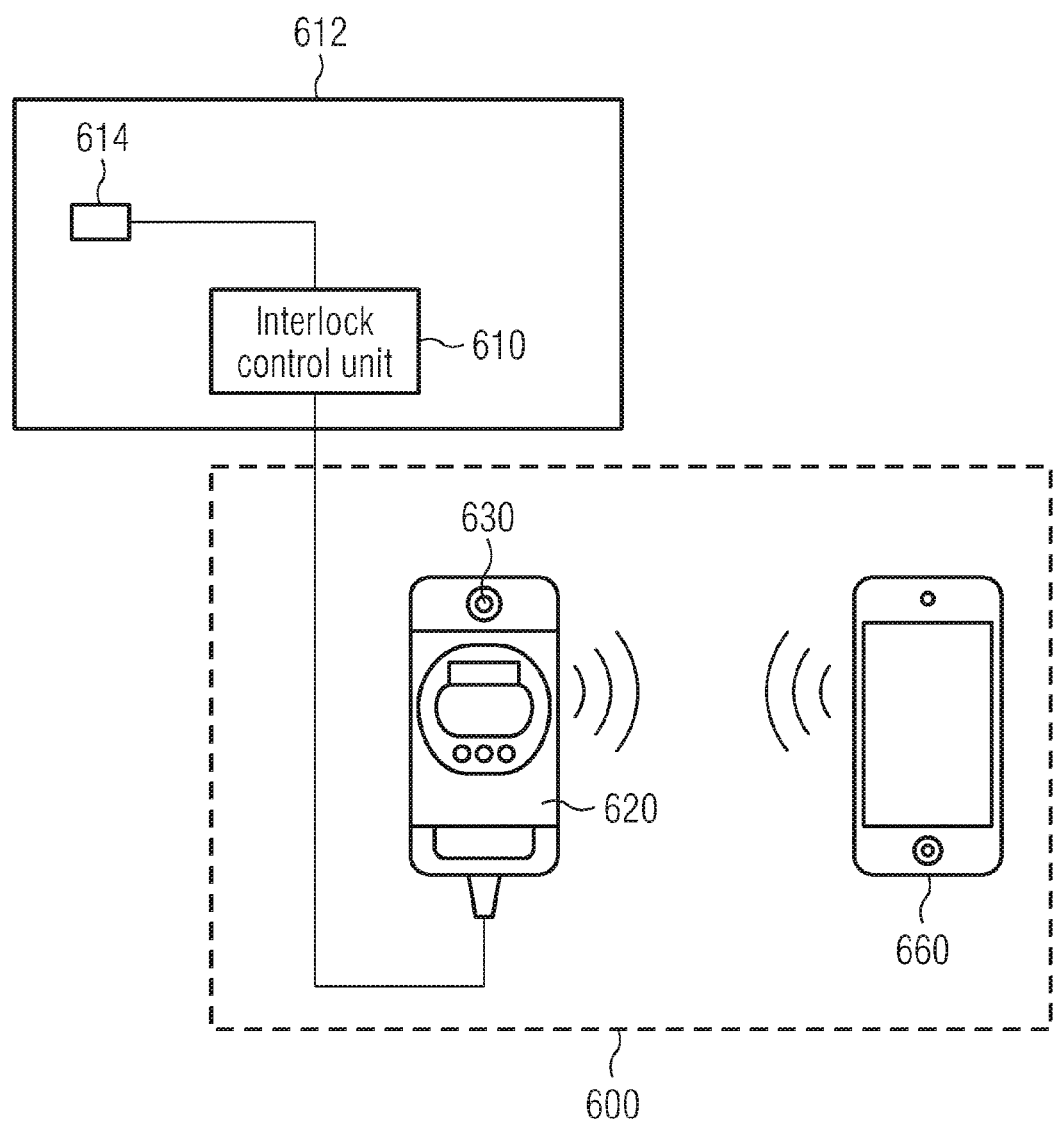
FIG. 9 is a diagram showing a blood alcohol content (BAC) processing system of a breath alcohol ignition interlock device in another example of the present disclosure.

FIG. 9 shows a blood alcohol content processing system 600 according to another example of the present disclosure. The breath alcohol ignition interlock device comprises at least two components: an input unit 620, which may be a handheld device mounted within reach of a driver's seat including a measuring display for measuring a volume of air exhaled by a user; and an interlock control unit 610 installed below a dashboard 612 of an automobile.

The user initially operates the ignition (not shown). Subsequently, the user is prompted to give a breath sample into the input device 620, by a request conveyed by the input device 620, e.g., by an acoustic signal or an LED lamp on the input device 620. The handheld device measures the alcohol concentration of the breath blown into a mouthpiece 630 of the input device 620, and a breath alcohol testing result is shown on a display.

If the value of alcohol in the breath measured is not above a previously programed threshold value, e.g., the legal limit of blood alcohol concentration for a driver, the control device releases a starting current to the automobile's ignition switch 614. Thus the engine may be started. However, if a too high concentration of breath alcohol is measured, the interlock control unit blocks the starting current and thus the start function of the engine.

The blood alcohol content processing system 600 comprises the input device 620 and a processing device 660. Just as in the previous example, the input device 620 and the processing device 660 may engage with one another to measure and evaluate the attributes of airflow of a sample of air given by a user into the input device 620. The software application is run on the processing device 660 in the same manner, thus assuring that a proper sample of air will be given by a user for the breath alcohol ignition interlock device. FIG. 9 indicates a wireless connection between the input device 620 and the processing device 660, but the connection may be wired.

Figure 10:
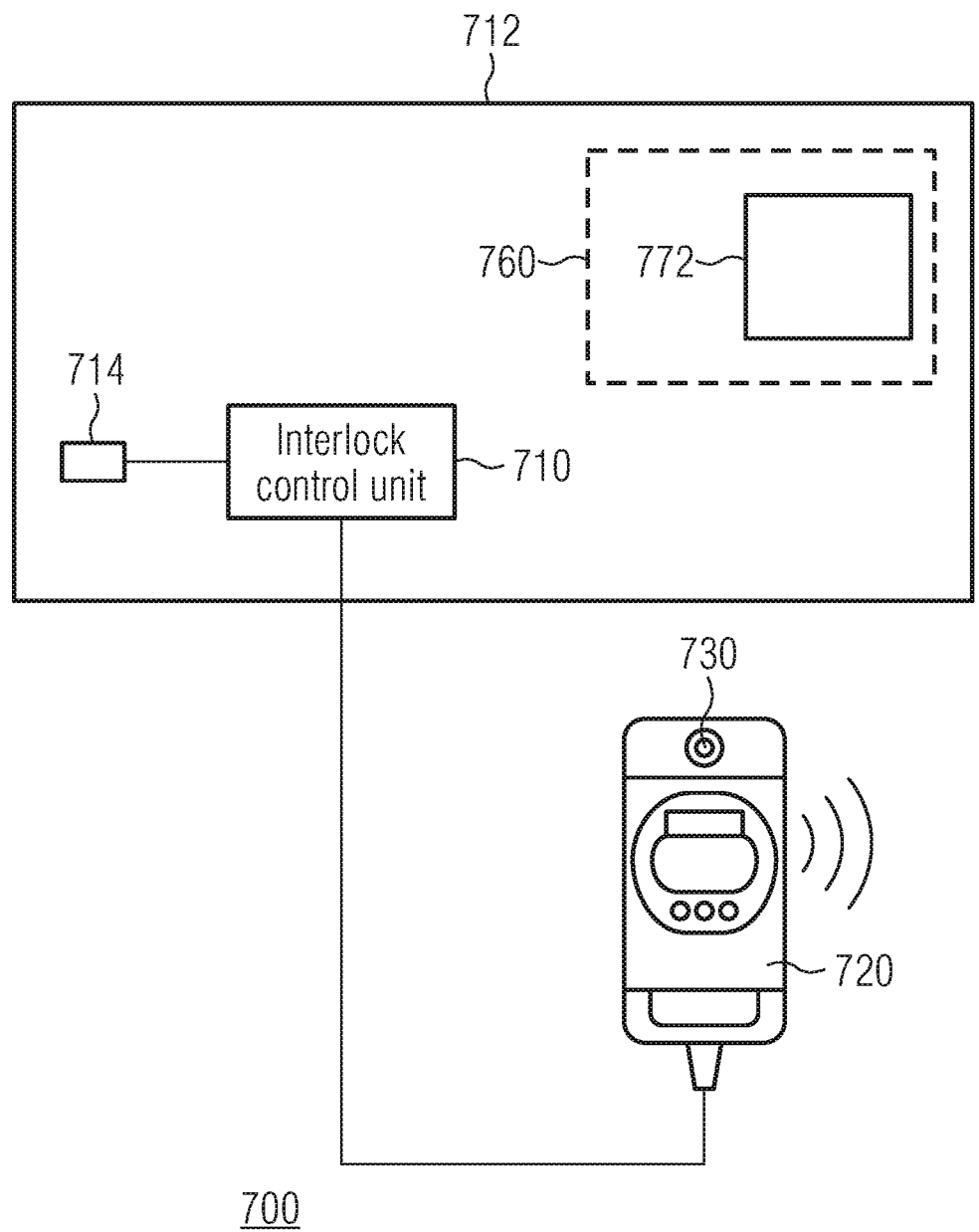
FIG. 10 is a diagram showing a blood alcohol content (BAC) processing system of a breath alcohol ignition interlock device with navigational panel display in another example of the present disclosure.

FIG. 10 shows a blood alcohol content processing system 700 according to another example of the present disclosure. Like the previous example, a breath alcohol ignition interlock device is utilized with an input unit 720, which may be a handheld device mounted within reach of a driver's seat including a measuring display for measuring a volume of air exhaled by a user; and an interlock control unit 710 installed below a dashboard 712 of an automobile to unlock an ignition switch 714. Another variation is presented that realizes a processing device 760 integrated with or connected to the automobile itself. The software application may be run by some processing means embedded within the automobile, and the user interface of the software application may be displayed on a display 772, e.g., on a vehicle navigational system.

FIG. 11 shows a blood alcohol content processing system 800 similar to that of the blood alcohol content processing system 600. A processing device 820 may be attached to the automobile through a front panel (not shown) via a USB port or the like. In the example, an indirect connection between the input device 820 and the processing device 860 may be established, and the software application may be successfully run with data transferred using an automobile's internal circuitry as an intermediary device.

Figure 12A:
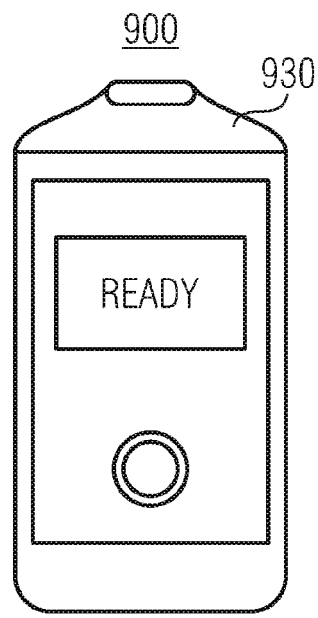
FIG. 12A is a diagram showing a front end of an integrated blood alcohol content (BAC) processing system in another example of the present disclosure.
Figure 12B:
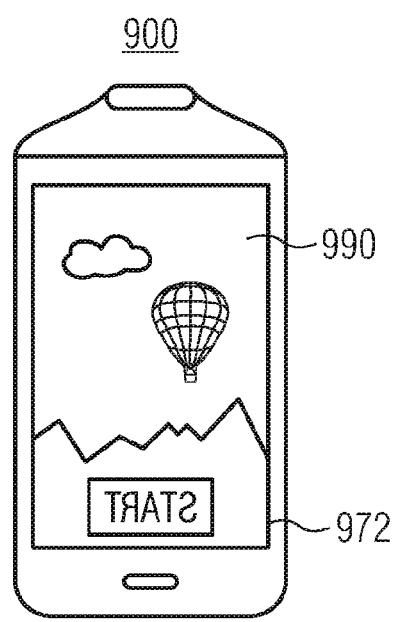
FIG. 12B is a diagram showing a back end of an integrated blood alcohol content (BAC) processing system in another example of the present disclosure.

Another example given by the present disclosure is an integrated blood alcohol content processing system 900, whereby an input device and a processing device are combined. FIGS. 12A and 12B show an example of an integrated system according to the present disclosure. The components of an input device and processing device, such as memory, an application processor, etc., may be implemented within the system 900. A software application may be started and displayed on a display 972 on, e.g., the back-side of the device such that when a user blows into a mouthpiece 930 on the front-side of the device, the software application for measuring the breath of a blood alcohol test may be properly implemented. A further example is given whereby the software application displays each of the states 990 with a mirror image effect. This effect may be implemented in any of the above examples. That is, the user interface of the software application is displayed as a mirror-image of its normal operational state. Thus, a virtual or animated image of a state 990 may be able to be seen and properly comprehended by a user when viewed in a rear-view mirror of an automobile, for example.

The aspects and features mentioned and described together with one or more of the previously detailed examples and figures, may as well be combined with one or more of the other examples in order to replace a like feature of the other example or in order to additionally introduce the feature to the other example.

Examples may further be or relate to a computer program having a program code for performing one or more of the above methods, when the computer program is executed on a computer or processor. Steps, operations or processes of various above-described methods may be performed by programmed computers or processors. Examples may also cover program storage devices such as digital data storage media, which are machine, processor or computer readable and encode machine-executable, processor-executable or computer-executable programs of instructions. The instructions perform or cause performing some or all of the acts of the above-described methods. The program storage devices may comprise or be, for instance, digital memories, magnetic storage media such as magnetic disks and magnetic tapes, hard drives, or optically readable digital data storage media. Further examples may also cover computers, processors or control units programmed to perform the acts of the above-described methods or (field) programmable logic arrays ((F)PLAs) or (field) programmable gate arrays ((F)PGAs), programmed to perform the acts of the above-described methods.

The description and drawings merely illustrate the principles of the disclosure. Furthermore, all examples recited herein are principally intended expressly to be only for pedagogical purposes to aid the reader in understanding the principles of the disclosure and the concepts contributed by the inventor(s) to furthering the art. All statements herein reciting principles, aspects, and examples of the disclosure, as well as specific examples thereof, are intended to encompass equivalents thereof A functional block denoted as "means for . . . " performing a certain function may refer to a circuit that is configured to perform a certain function. Hence, a "means for s.th." may be implemented as a "means configured to or suited for s.th.", such as a device or a circuit configured to or suited for the respective task.

Functions of various elements shown in the figures, including any functional blocks labeled as "means", "means for providing a sensor signal", "means for generating a transmit signal.", etc., may be implemented in the form of dedicated hardware, such as "a signal provider", "a signal processing unit", "a processor", "a controller", etc. as well as hardware capable of executing software in association with appropriate software. When provided by a processor, the functions may be provided by a single dedicated processor, by a single shared processor, or by a plurality of individual processors, some of which or all of which may be shared. However, the term "processor" or "controller" is by far not limited to hardware exclusively capable of executing software, but may include digital signal processor (DSP) hardware, network processor, application specific integrated circuit (ASIC), field programmable gate array (FPGA), read only memory (ROM) for storing software, random access memory (RAM), and non-volatile storage. Other hardware, conventional and/or custom, may also be included.

A block diagram may, for instance, illustrate a high-level circuit diagram implementing the principles of the disclosure. Similarly, a flow chart, a flow diagram, a state transition diagram, a pseudo code, and the like may represent various processes, operations or steps, which may, for instance, be substantially represented in computer readable medium and so executed by a computer or processor, whether or not such computer or processor is explicitly shown. Methods disclosed in the specification or in the claims may be implemented by a device having means for performing each of the respective acts of these methods.

It is to be understood that the disclosure of multiple acts, processes, operations, steps or functions disclosed in the specification or claims may not be construed as to be within the specific order, unless explicitly or implicitly stated otherwise, for instance for technical reasons. Therefore, the disclosure of multiple acts or functions will not limit these to a particular order unless such acts or functions are not interchangeable for technical reasons. Furthermore, in some examples a single act, function, process, operation or step may include or may be broken into multiple sub-acts, -functions, -processes, -operations or -steps, respectively. Such sub acts may be included and part of the disclosure of this single act unless explicitly excluded.

Furthermore, the following claims are hereby incorporated into the detailed description, where each claim may stand on its own as a separate example. While each claim may stand on its own as a separate example, it is to be noted that—although a dependent claim may refer in the claims to a specific combination with one or more other claims—other examples may also include a combination of the dependent claim with the subject matter of each other dependent or independent claim. Such combinations are explicitly proposed herein unless it is stated that a specific combination is not intended. Furthermore, it is intended to include also features of a claim to any other independent claim even if this claim is not directly made dependent to the independent claim.

What is claimed is:

1. A method for monitoring breath, the method comprising:
    measuring one or more attributes of airflow through an input device, by a flow sensor within the input device, of air blown into said input device by an expelling action of a user;
    transmitting the attributes of airflow from the input device to a processing device, including a processor and communication terminal;
    communicating, via the communication terminal, a first state output to the user while the air is blown into said input device; and
    determining, by the processor of the processing device, whether each of the attributes of airflow is within a respective threshold range, wherein, if a respective threshold range is met, the communication terminal communicates a second state output to the user, the first state output and the second state output comprising a graphical image analogous to a real air movement event based on the attributes of airflow from said flow sensor, wherein the graphical image is continuously displayed on a display of the communication terminal from a start of air blown into said input device to an end of air blown into said input device, wherein a state of the graphical image changes based on said attributes of airflow from said input device.

2. The method of claim 1, wherein the attributes of airflow measured by the flow sensor include at least the volume of air or the duration of time air is blown, as detected by the flow sensor, wherein the graphical image comprises an image of a candle, wherein the candle comprises a flame in the first state output, wherein the flame of the candle is shown in an extinguished state in the second state output.

3. The method of claim 1, further comprising the step of:
    transmitting initialization data, including the respective threshold range of an attribute of airflow, from the input device to the processing device before measuring said attribute of airflow from the input device, wherein the graphical image comprises an image of a hot air balloon, wherein a height of said hot air balloon changes based on said attributes of airflow from said flow sensor.

4. The method of claim 1, wherein the transmitting of attributes of airflow from the input device to the processing device is in real-time, while air is detected and measured by the flow sensor as being blown into the input device, wherein said graphical image comprises an image of a dandelion, wherein seeds of said dandelion are dispersed based on said attributes of airflow from said flow sensor.

5. The method of claim 1, wherein the transmitting of attributes of airflow from the input device to the processing device is done wirelessly.

6. The method of claim 1, wherein the processing device further includes a haptic circuit component, wherein the communication terminal communicates the first state output or the second state output to a user via kinesthetic communication through the haptic circuit component, wherein the graphical image comprises an image of an airplane, wherein a position of the airplane changes based on said attributes of airflow from said flow sensor.

7. The method of claim 1, wherein the processing device further includes an audio circuit component, the communication terminal communicating the first state output or the second state output to a user via auditory communication through the audio circuit component, the graphical image comprising an image involving one of air, breath, inflation and blowing.

8. The method of claim 1, wherein the processing device further includes a display circuit component, the communication terminal communicating the first state output or the second state output to a user via visual communication through the display circuit component, said graphical image comprising an image of a circle, wherein a size of said circle changes based on said attributes of airflow from said flow sensor.

9. The method of claim 1, wherein the processing device is integrally formed with the input device as included in a breath analyzing system.

10. The method of claim 9, wherein the breath analyzing system further comprises a display circuit component, which is located on a surface of the breath analyzing system that is opposite to the location of an input port of the input device, and wherein the communication terminal communicates the first state output or the second state output to a user via visual communication through the display circuit component.

11. The method of claim 10, wherein the visual communication is displayed as such that the first state output or second state output are displayed with a mirror image effect.

12. A mobile terminal for monitoring breath, the mobile terminal comprising:
an I/O processing circuit component that receives transmission of attributes of airflow from an input device, including a flow sensor, of air blown into said input device by an expelling action of a user;
a communication terminal, which includes an interface circuit and communicates, via the interface circuit, a first state output to the user while air is blown into said input device, the communication terminal comprising a display; and
a processor, which processes whether each of the attributes of airflow is within a respective threshold range, wherein, if a respective threshold range is met, the processor transmits to the communication terminal validation of a met threshold range, and the communication terminal communicates via the interface circuit a second state output to a user, the first state output and the second state output comprising a graphical image analogous to a real air movement event based on said attributes of airflow from said input device, wherein the graphical image is continuously displayed on a display of the communication terminal from a start of air blown into said input device to an end of air blown into said input device, where a state of the graphical image changes based on said attributes of airflow from said input device.

13. The mobile terminal of claim 12, wherein the attributes of airflow measured by the flow sensor include at least the volume of air or the duration of time air is blown, as detected by the flow sensor, the graphical image comprising an image involving one of air, breath, inflation and blowing.

14. The mobile terminal of claim 12, wherein the processor initializes the respective threshold range of the attribute of airflow from an initialization signal received from the input device to the I/O processing circuit component before the I/O processing circuit component receives transmission of attributes of airflow as measured by the flow sensor of the input device, wherein the graphical image comprises an image of a candle, wherein the candle comprises a flame in the first state output, wherein the flame of the candle is shown in an extinguished state in the second state output.

15. The mobile terminal of claim 12, wherein the I/O processing circuit component further includes a wireless transmission component to wirelessly receive or transmit signals from or to the input device.

16. The mobile terminal of claim 12, wherein the mobile terminal is integrally formed with the input device.

17. The mobile terminal of claim 16, wherein the interface circuit comprises a display circuit component, which is located on a surface of the breath analyzing system that is opposite to the location of an input port of the input device, and wherein the communication terminal communicates the first state output or the second state output to a user via visual communication through the display circuit component.

18. The mobile terminal of claim 17, wherein the visual communication is displayed as such that the first state output or second state output are displayed with a mirror image effect.

19. A non-transitory, computer-readable medium for monitoring breath, the computer-readable medium comprising instructions stored thereon, that when executed on a processor, perform the steps of:
receiving an electronic transmission of one or more attributes of airflow from an input device, which measures the attributes of airflow by a flow sensor within the input device of air blown into said input device by an expelling action of a user, to a mobile device, including the processor and a communication terminal;
communicating, via the communication terminal, a first state output to the user while the air is blown into said input device; and
determining, by the processor, whether each of the attributes of airflow is within a respective threshold range, wherein, if a respective threshold range is met, the communication terminal communicates a second state output to the user, the first state output and the second state output comprising a graphical image analogous to a real air movement event based on said attributes of airflow from said input device, wherein the graphical image is continuously displayed on a display of the communication terminal from a start of air blown into said input device to an end of air blown into said input device, wherein a state of the graphical image changes based on said attributes of airflow from said input device.

20. The non-transitory, computer-readable medium of claim 19, wherein the graphical image comprises an image of a candle having a flame, wherein a state of the flame changes based on said attributes of airflow from said input device.

* * * * *